Figure 1:
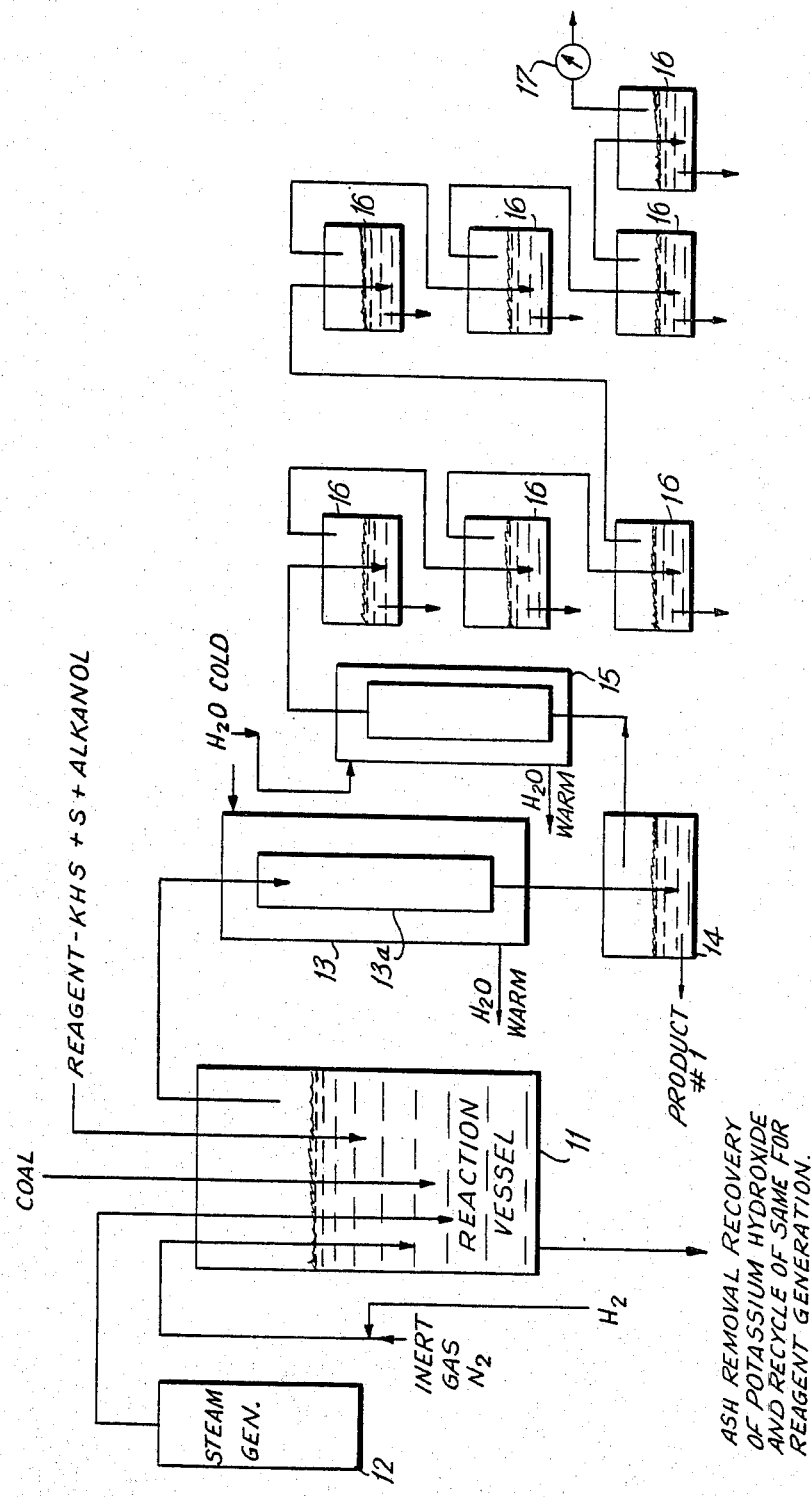

United States Patent [19]

Swanson

[11] 4,366,044
[45] * Dec. 28, 1982

[54] PROCESS FOR CONVERSION OF COAL TO HYDROCARBON AND OTHER VALUES

[76] Inventor: Rollan Swanson, c/o Chemroll Enterprises, Inc., 100 Wall St., New York, N.Y. 10036

[*] Notice: The portion of the term of this patent subsequent to Dec. 28, 1999, has been disclaimed.

[21] Appl. No.: 220,021

[22] Filed: Jan. 5, 1981

Related U.S. Application Data

[63] Continuation-in-part of Ser. No. 63,824, Aug. 6, 1979, abandoned, Ser. No. 114,207, Jan. 22, 1980, and Ser. No. 140,604, Apr. 15, 1980.

[51] Int. Cl.³ .............. C10G 1/06; C10G 1/00; C10G 47/02; C10J 3/16
[52] U.S. Cl. .................... 208/10; 208/8 R; 208/8 LE; 208/108; 48/202; 44/1 SR
[58] Field of Search ............ 208/8 R, 8 LE, 10, 108; 44/1 SR; 63/824; 201/2.5; 48/202

[56] References Cited

U.S. PATENT DOCUMENTS

| | | | |
|---|---|---|---|
| 1,899,042 | 2/1933 | Malisoff | 208/209 |
| 1,904,586 | 4/1933 | Winkler et al. | 208/8 R |
| 2,379,654 | 7/1945 | Royer | 208/213 |
| 3,248,303 | 4/1966 | Doying | 201/2.5 X |
| 3,383,304 | 5/1963 | Mattox et al. | 208/230 |
| 3,387,941 | 6/1968 | Murphy et al. | 208/213 |
| 3,474,028 | 10/1969 | Bulian et al. | 208/230 |
| 3,725,250 | 4/1973 | Wilson et al. | 208/208 R |
| 3,846,275 | 11/1974 | Urban | 208/10 |
| 3,847,567 | 11/1974 | Kalina et al. | 48/202 |
| 3,864,097 | 2/1975 | Urban | 201/2.5 X |
| 4,119,528 | 10/1978 | Baird et al. | 208/108 |
| 4,147,611 | 4/1979 | Miasek et al. | 208/235 X |
| 4,147,612 | 4/1979 | Miasek et al. | 208/235 X |
| 4,155,717 | 5/1979 | Sun et al. | 44/1 SR |
| 4,230,184 | 10/1980 | Blytas | 208/230 |
| 4,233,034 | 11/1980 | Miller et al. | 44/1 SR |

Primary Examiner—Delbert E. Gantz
Assistant Examiner—William G. Wright
Attorney, Agent, or Firm—Fred A. Keire

[57] ABSTRACT

A process for converting coals to hydrocarbon values, by intimately contacting coals such as lignite coal with a reagent, e.g., an alkali metal sulfide or polysulfide or an alkali metal hydrosulfide, in the presence of steam, or a combination of steam and hydrogen sulfide, at temperatures between 65° C. to 450° C.; liquid and gaseous hydrocarbons of preselected compositions may be produced; these are useful as fuel, or as chemical starting materials, e.g., for upgrading fuel or making industrial chemicals.

51 Claims, 2 Drawing Figures

PROCESS FOR CONVERSION OF COAL TO HYDROCARBON AND OTHER VALUES

This application is a continuation-in-part of my Applications Ser. No. 063,824 filed Aug. 6, 1979 now abandoned, Application Ser. No. 114,207 filed Jan. 22, 1980; and Application Ser. No. 140,604 filed Apr. 15, 1980.

In my first filed application, I disclose a method for preparing an alkali metal reagent and a reaction based on this reagent with oxygen, nitrogen and sulfur in coal. The essential disclosure and claims of the above application have now been incorporated herein.

In Application Ser. No. 114,207, I disclose the utilization of the method disclosed in the first filed application to coals of various rank and peat and the use of water or steam in the process which may be practiced batchwise or continuously. Application Ser. No. 114,207 contains also a disclosure for varying the conditions so as to obtain a product mix by use of different temperatures, reagents, rank of coal as well as reaction stages. In Application Ser. No. 114,207, I disclose addition of sulfur to stabilize a reagent as a less hydrolyzed polysulfide.

In application Ser. No. 140,604, I disclose a number of methods for preparing reagents, the stabilization of these reagents by employing hydrogen sulfide in hydrotreating carbonaceous materials and stagewise reactions. I have now found that besides stabilization of the reagent, for coals and peat, the addition of hydrogen sulfide surprisingly provides heretofore unknown, further benefits based on the difference in the chemistry of coals or peat as distinguished from the carbonaceous materials disclosed in that application.

The disclosure of each of the above applications is incorporated by reference herein.

This invention incorporates further developments in the inventions disclosed in the above applications and relates to conversion of coal to various useful component parts thereof, either, principally gaseous component parts or various proportions of gaseous and liquid component parts, including substantially liquid products. This invention further describes conversion of these gaseous components into other distillates; more particularly, this invention relates to the conversion of coal to desired conversion products thereof such as hydrocarbons in liquid or gaseous form by reacting coal in one or more stages with a particular reagent therefor, which may be the same or different for each of the stages, in the presence of water, steam, sulfur and/or hydrogen sulfide, at a low to moderate temperature and between atmospheric pressure and pressure less than 5 psig.

Still further, this invention relates to conversion of coal to various preselected component cuts thereof, either principally gaseous component parts, gaseous and liquid components or principally liquid components by means of specific reagents, whereby coal, or peat, in the presence of this reagent, water, steam, sulfur and/or hydrogen sulfide, is converted into useful breakdown materials of coal or peat. These breakdown materials are either principally gaseous hydrocarbons obtained in a single stage reaction or principally liquid hydrocarbons obtained in a single stage, or the gaseous and light liquid products ("light" means low boiling point liquid), from a single stage. These products may be further reacted in one or more additional stages to obtain liquid distillates. Ultimately, at the high temperatures, coal in the presence of the reagent and steam, causes production of some hydrogen. The residue of the coal comprises ash and reagent from which the reagent and other ash values may be recovered and reused.

BACKGROUND OF THE INVENTION

It has become increasingly evident that liquid and gaseous hydrocarbon sources such as petroleum and natural gas are being depleted at such rapid rate than an intensive effort is needed to meet anticipated future needs for obtaining substitute energy, feedstock, or chemical starting materials. One of the most readily available sources of hydrocarbon materials is coal. Heretofore, there has been no ready means, without extensive capital investment on economically justifiable basis, to produce hydrocarbons from coal. Although various processes are known for conversion of coal at high temperatures, such as high temperature i.e. above 600° C., high pressure e.g. above 25 atmospheres coal gasification, there has been no readily available lower-temperature, low-pressure process which would readily convert coal into its component hydrocarbons.

PRIOR ART

In considering the present invention, I am aware of the following patents: U.S. Pat. Nos. 1,300,816; 1,413,005; 1,729,943; 1,904,586; 1,938,672; 1,974,724; 2,145,657; 2,950,245; 3,112,257; 3,185,641; 3,252,774; 3,368,875; 3,354,081; 3,382,168; 3,483,119; 3,553,279; 3,565,792; 3,617,529; 3,663,431; 3,745,109; 3,787,315; 3,788,978; 3,816,298; 3,926,775; 3,933,475; 3,944,480; 3,960,513; 3,957,503; 4,003,823; 4,007,109; 4,018,572; 4,030,893; 4,057,422; 4,078,917; 4,119,528; 4,147,611; 4,147,612; 4,155,717; 4,160,721 and 4,210,526.

In considering the present invention, I am also aware of the following literature references:

Letoffe, et al., Determination des Enthalpies de Formation des Polysulfures de Potassium, *Journal de Chimie Physique*, 71, pp 427–430, 1974;

John S. Thomas and A. Rule (other articles of this series were authored by Thomas and Riding) The Polysulfides of the Alkali Metals, *Journal Chemical Soc.*, Part 3 pp 1063 et seq., 1973;

Blitz and Wilke-Dorfurt, *Z. Anorg. Chem.*, vol. 48, pp 297, 1906 (also see Ber., 53, pp 43, 1905);

van Krevelen, et al., *Fuel*, 38, 256, 1959;

B. K. Mazumdar, et al., *Fuel*, 41, 121, 1962;

Hugot, *Ann. Chim Phys.*, 21, 72, 1900;

W. Klemm, *Z. Anorg. Chemm.*, pp 241, 281, 1939;

F. W. Bergstrom, *J. Amer. Chem. Soc.*, 147, 1926;

F. Feher and H. Berthold, *Z. Anorg. Chem.*, pp 247, 1953;

Thomas and Rule, *J. Chem. Soc.*, 2819, 1914;

R. L. Erbeck, *Dissert. Abstract*, Ann Arbor, Mich. 3254, 21, 1961;

Renegade and Costeanu, *Bull. soc. Chim.*, 15, 721, 1911;

Sabbatier, *Ann. Chim. Phys.* 22, 5, 1881;

Marrony, *J. Chim. Phys.*, 56, 214, 221, 1959;

MMe Aline Auroux, *C.R. Acad. Soc. Paris*, 274 pp 1297 to 1300, March 1972;

Kuster und Herberlein "Beitrage zur Kenntnise der Polysulfide" *Z. anorg Chem.*, pp 53–84, November 1904.

GENERAL DESCRIPTION OF THE INVENTION

It has now been found that when coal is treated with a paticular reagent, it can be converted in the presence of this reagent and in the presence of water and/or steam and/or hydrogen sulfide to various hydrocarbon fractions either principally gaseous hydrocarbon fractions of one to five carbon atoms ($C_1$ to $C_5$), e.g., methane, ethane, ethene, etc., or principally liquid distillates or in a ratio which is for practical purposes between these limits. Hydrogen is also co-produced.

Further, it has been found that when this conversion is being carried out at different temperatures, i.e., using steam and coal at set steps, at elevated temperatures, the proportion of the various hydrocarbons obtained from the same coal can be changed. At lower temperatures more volatile liquid hydrocarbons will be produced. At higher temperatures, more or principally gaseous hydrocarbons will be produced; moreover when using a different reagent in another reactor the gaseous hydrocarbons in the presence of steam and hydrogen sulfide may be further reacted to obtain different hydrocarbons such as liquid or gaseous hydrocarbons. It has also been discovered that by changing the reagent and using apparently anhydrous and eutectic mixtures of sulfides as further explained herein the above conditions may be reversed.

Still further, it has been found that various coals, that is, lignites of various compositions, bituminous and sub-bituminous coals show different distillation points although the production of the liquid and gaseous hydrocarbons will still take place. Higher value (rank) coals give more liquid hydrocarbon distillate than do lower value coals while other process or reagent modifications, as further explained herein, allow the obtention of more liquid distillates.

In general terms, it is believed that when the alcoholic solution of KHS by itself (or with sulfur) is being added to the coal, a reaction takes place as follows:

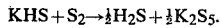

From the above it follows that KHS may be used without sulfur addition. However, sulfur tends to stabilize KHS as a less hydrolyzed polysulfide. Further, it has been surprisingly found that hydrogen sulfide addition is considerably more beneficial than sulfur addition because hydrogen sulfide stabilizes the reagent more effectively, and helps in conversion of the thiosulfate or the tetrathionate and $2e=2$ thiosulfate ions formed.

There is some breakdown of KHS to $K_2S$ in the presence of water. This breakdown is partial. Hence, in hydrogenating coal, both KHS and $K_2S$ should be present in the reaction. When sulfur is added, a less hydrolyzed, and therefore, a more water-stable polysulfide e.g. potassium pentasulfide is also provided.

Although the above reaction is shown for KHS, NaHS will also work, but appears to work best without elemental sulfur addition. It is also possible to use KHS or NaHS in dry state, i.e., without alcohol addition. NaHS is obtainable as an industrial bulk commodity, generally in a flake form with about 30% by weight of water in the bulk form.

It has further been found that when mixtures of alkali sulfides are reacted these may be added in liquid state to coal to facilitate the reaction, e.g., such as mixtures of polysulfides or hydrates thereof.

When the $K_2S$ and various polysulfide species thereof, react with coal, these preferentially attack the oxygen, sulfur and nitrogen present in coal in a bound form to withdraw or abstract these components of coal. As derivative hydrocarbon components are forming in the presence of reagent steam or water, and hydrogen sulfide, the bond scission of the various coal constituent parts and abstraction of oxygen, nitrogen and sulfur, allow the introduction of hydrogen from water or hydrogen sulfide and thus the formation of hydroaromatic, aromatic and shorter chain aliphatic compounds. The severity of attack can be tailored from where the product is essentially gas to where the product is essentially liquid, based on the reagent(s) employed and the operating conditions.

It has been found that oxygen must be present in the coal. For this purpose, low quality coals, such as lignites, are very suitable.

Figure 2:
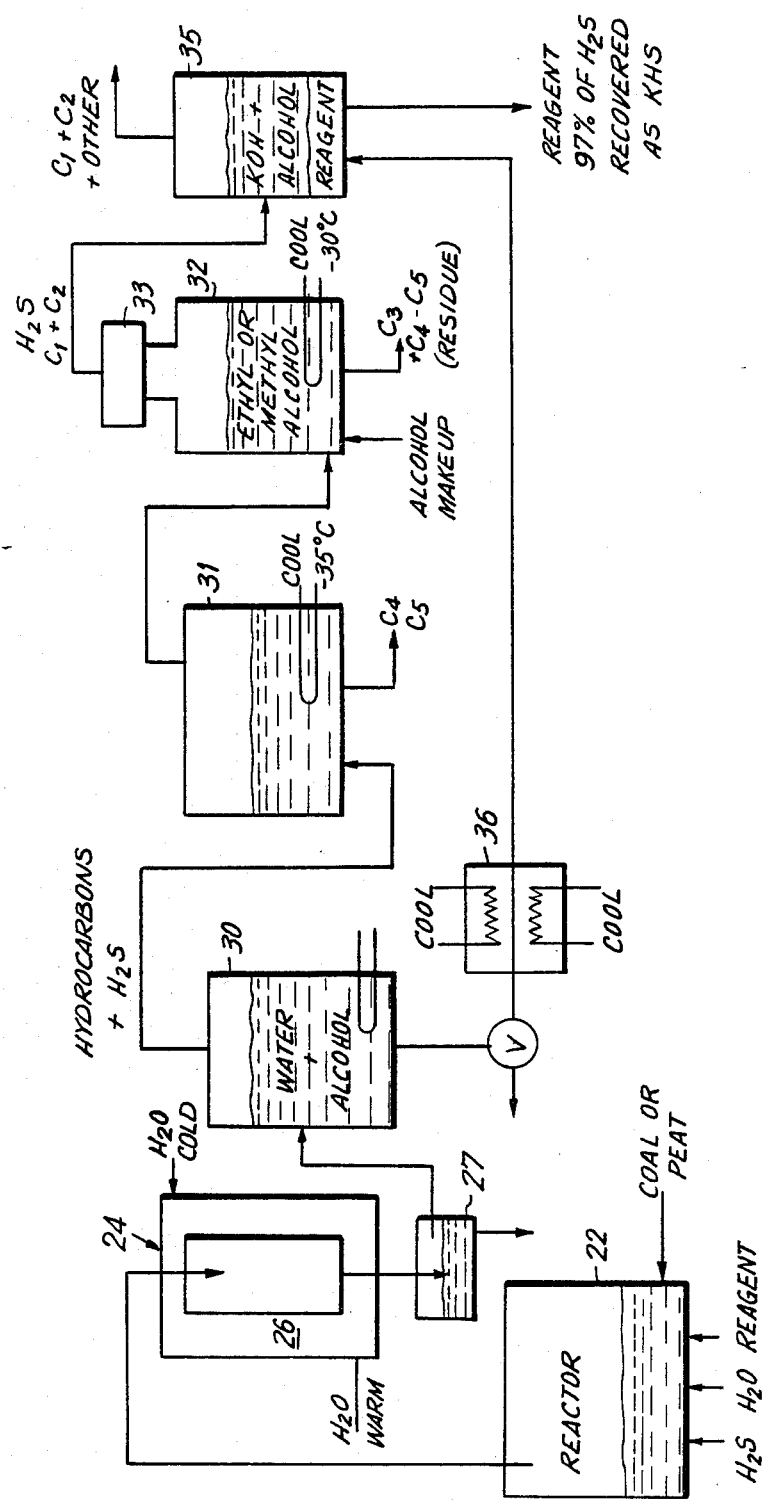

In order to illustrate further the present invention, schematic drawings are presented wherein:

FIG. 1 shows the schematic reaction train of the coal conversion and component recovery; and FIG. 2 illustrates, schematically, hydrogen sulfide recovery from a gaseous value recovery train.

Turning now to FIG. 1, the reaction vessel 11 is typically a retort or a similar device in which coal in a finely ground stage is being fed. Typically, particle size of coal is up to ¼ inch for lignite and can be more, as the reaction is size independent. For bituminous or sub-bituminous coal, the particle size can be up to ¼ inch but is preferably about 1/32 of an inch. After the system has been first purged of any oxygen, by introducing inert gas, such as helium or nitrogen, etc., the reagent, as $K_2S$ or KHS (or equivalent) in alkanol as a water solution, or a "dry" composition i.e. in solid form is introduced therein The system is then closed and the temperature is elevated to 78° C. (for methanol) at which temperature the alkanol from the reagent is distilled. If ethanol is used the temperature is 92° C. As the inert gas, i.e., nitrogen, helium or hydrogen, provide the agitation, the continuous expulsion of water continues along with the expulsion of the alkanol. Typically, the alkanol is methanol or ethanol, although higher 1-alkanols may be used such as alkanols up to 4 carbon atoms.

Once the desired operating temperature is reached (after alkanol distillation—if used in the process) and steam and hydrogen sulfide at an appropriate temperature is being introduced into the system, the inert gas such as nitrogen, first used to purge the system of oxygen, may no longer be needed. The steam vessel 12 is provided with means for heating water, or auxiliary heating may be supplied such as by heating the line from the steam generator 12 to reaction vessel 11. Hydrogen sulfide may be introduced through the steam line.

An appropriate means for monitoring or controlling the reaction in the reaction vessel may also be provided such as heating or cooling coils, temperature gauges, heat control elements, stirring devices, etc. The reaction vessel may also be externally heated.

The reaction products from the reaction vessel are introduced into the condenser 13, which may be of a refluxing type with the in and out water temperature adjusted to condense the heavier fraction first coming over from the coal. The heavier fraction may condense on the walls of the condenser device 13a and then descend downwardly until received in the bottom collector 14 from which these liquid products may be removed, recovered and analyzed from time to time.

From the bottom collector 14, the gaseous effluent is then sent on to a second condenser 15 where the gaseous products are further cooled and introduced into the scrubbers 16. In these scrubbers 16 appropriate scrubbing liquids are kept so as to collect the desired product fraction in each of the scrubber liquids. On an industrial scale, separation in a distillation column may be more practical.

The nonsolubilized but scrubbed component, in it gaseous from, in turn, is introduced into the next scrubber, from which further components are separated (as will be further explained herein). Although seven scrubbing stations have been shown, the number depends on the gaseous fractions sought to be recovered. Hence, the number of the scrubbing sections may be increased or decreased. The final gaseous fraction is metered by meter 17 and may be collected and treated such as by further scrubbing and purification, i.e., distillation, or it may be used directly.

As it is well understood, inasmuch as the gaseous fraction from the gasification of coals is a fairly narrow fraction consisting in the major part of gaseous fractions having from 1 to 6 carbon atoms or near liquids thereof, fractionation may also be employed for recovery of the various reaction products. Typical fractionation means are such as a distillation tower and molecular sieve separation means. These separation and distillation means are well known to those skilled in the art and need not be illustrated.

For purposes of this invention, however, an embodiment is shown which allows the separation of various fractions based on the solubilities of the hydrocarbons having from 1 to 6 carbon atoms.

This process may be carried out continuously. Thus, the separation function for the various reactants (such as the alcohol based reagent) may be effected in such a manner that the system may operate continuously with continuous introduction of reagents, coal, and steam and continuous removal of product. Under those conditions, inert gas purging may not be necessary, but atmospheric oxygen must be expelled from coal prior to introduction in the reactor. The reactor and ancillary equipment must be free from oxygen. From each of the scrubbers 16 the dissolved component may be separated by conventional means and the liquid used therein separated therefrom.

Turning now to the solubilities which have been given herein, typically, these are for the indicated gas at normal room temperature defined as 72° F. Inasmuch as the scrubbing process can be operated at room temperature and at near atmospheric pressure, the solubilities are intended to be for those conditions. It is noted that higher pressures may also be used such as in a distillation train so as to avoid any excessively low temperatures. Again, when the pressure conditions are changed, the recovery which may be effected at the changed pressure is well understood by those skilled in the distillation art.

Based on the well known solubility factors, such as available from reference handbooks, these are listed for the hydrocarbons recovered from the system. Solubilities of $C_1$–$C_6$ hydrocarbons are as follows:

Ethane is soluble in ether, slightly soluble in alcohol, acetone and benzene and insoluble in water. Ethane is soluble in benzene, slightly soluble in alcohol and acetone and insoluble in water. Propane is soluble in water and in alcohol, very soluble in ether and benzene and slightly soluble in acetone. It is also very soluble in chloroform. Propene in very soluble in water, in alcohol and in acetic acid. Butane is very soluble in alcohol and ether and chloroform and is soluble in water. Butene (1− & 2−) is very soluble in alcohol and ether, is soluble in benzene and insoluble in water. 1−, 2−, and transpentene is miscible in alcohol and ether, very soluble in dilute sulfuric acid, and soluble in benzene but insoluble in water. Pentene is miscible in alcohol, ether, acetone, benzene, chloroform and heptane slightly soluble in water. Hexane is soluble in ether and chloroform and very soluble in alcohol and insoluble in water. Hexenes (1−, 2−, trans, 3−) are soluble in alcohol, ether, benzene, chloroform, pet. ethers, and insoluble in water. Methane is soluble in water, alcohol, ether, benzene, methanol, and toluene and slightly soluble in acetone.

The reagent such as the potassium hydrosulfide or sodium hydrosulfide (the last is reconstituted solely in water solution) or a sulfide or a polysulfide thereof is reconstituted such as in one of the reaction vessels when the scrubbing liquid therein is alkanolic KOH, or water solution NaOH to form either the appropriate sulfide or hydrosulfide depending on the amount of $H_2S$ to react with the hydroxide. Potassium hydrosulfide may also be reconstituted in water solution. Typically, at those conditions the reagent will precipitate as a white precipitate, e.g., of the formula $K_2S$ (hydrate) or $Na_2S$ (hydrate). In ethanol or higher alkanols the only slightly soluble alkali metal sulfide can be removed from the system by merely withdrawing the precipitate from the scrubber.

The ash remaining in the reaction vessel 11 is appropriately removed therefrom and worked up such as by dissolving the solubles therein and extracting, e.g. potassium therefrom based on the differential solubility of calcium hydroxide and potassium hydroxide, that is, extracting potassium with calcium hydroxide, precipitating calcium sulfate and removing potassium hydroxide. Sodium hydroxide is present in the ash in lesser quantities and may be removed in the same or different manner, as it is well known in the art. As sodium is present in coal in considerably smaller proportions than potassium, sodium may have to be augmented during the continuous process if sodium based reagent is used. There is sufficient amount of potassium present in coal ash.

As it is evident from the above, at lower temperatures, for lignite such as given in the example (to follow) the reaction provides a hydrocarbon fraction which is in the $C_3$–$C_6$ hydrocarbon range with the fraction having an average of $C_4$ predominating. This fraction is typically recovered up to about 120° C. At 220° C. the methane through butane fraction is being produced including the corresponding double bond unsaturates. At 360° to 450° C., typically ethene and copious amounts of hydrogen are being produced. In order to assure that no hydrogen sulfide is being expelled, the product stream is scrubbed in an alkali metal e.g. potassium or sodium hydroxide alkanolic or water solutions, respectively, at near saturated conditions. The hydrogen sulfide reacts with the hydroxide to regenerate the reagent, i.e., $K_2S$ and $Na_2S$ and in presence of water regenerates KHS and and NaHS. In the thus scrubbed gas stream, hydrogen sulfide is present in a very small amount e.g. less than 0.01%, by volume.

In FIG. 2, a schematic illustration of a hydrogen sulfide gas recovery is provided. A reactor 22, typically at 350° C. to 390° C. has been charged with coal, a reagent in liquid form, water, in the form of steam, and hydrogen sulfide gas. A cooling jacket 24, surrounding the condenser 26 facilitates the cooling of the reaction gases. The initial and heavier products are recovered from condenser bottoms 27. The gaseous products are sent on to vessel 30 in which water and alkanol (typically methane or ethane) are held.

Vessel 30 receives water or alkanol from the reactor when alkanol solubilized reagent is used. The mixture of water and alcohol in vessel 30 is kept below the boiling point of the mixture and thus the lighter gases pass through such as the $C_1$ to $C_5$ including hydrogen sulfide.

In vessel 31 the contents are cooled to about $-35°$ C. at which temperature liquid $C_4$ and $C_5$ are removed. While most of $C_4$ and $C_5$ fractions are removed in vessel 31, some still are carried over to vessel 32 where these are removed at $-30°$ C. with the $C_3$ fraction in ethanol or methanol. A fritted glass disk 33 removes any residual mist of these components. At this state substantially only $H_2S$ and $C_1$ and $C_2$ fractions are present in the gas stream which is then introduced into vessel containing KOH and alcohol, typically ethanol or methanol or water solution. Hydrogen sulfide therein reconstitutes the reagent, which is recovered as a precipitate, while the light fraction gases predominantly $C_1$ and $C_2$ pass. About 97% and more of $H_2S$ is recovered as a reagent component and may be reused. No $H_2S$ is vented to air. The alcohol-water fraction from vessel 30 is used to replenish the alcohol dragged out from vessel 35. However, this mixture must be cooled in heat exchanger 36.

The above illustration of the process as well as the invention herein is described by reference to the examples which are not intended as a limitation of the invention, but rather as an illustration of an embodiment thereof.

EXAMPLE 1

Fifty milliliters of a methanol solution of potassium hydrosulfide, containing 0.37 grams of potassium hydrosulfide/ml. were used as the base reagent. 71 grams of a lignite were used having a "dry ashless" content of 66% carbon, 3.97% hydrogen, 18.2% oxygen, and 0.9% nitrogen, by weight, plus a small amount of volatiles. The raw lignite contained 33% water and 9% dry ash. (The "as received" wet analysis was 6% ash). The organic sulfur content of this lignite was 0.69% and the pyritic sulfur content was unknown.

The run was made with lignite which had been dried for 2 hours at 135° C. and with lignite which had not been dried. The principal difference between the dry and wet lignite was a production of very light hydrocarbon gases from the wet lignite at temperatures below the boiling point of water during the period that the temperature was being elevated. Water from the lignite provided the hydrogen for this production of hydrocarbon distillate. In other respects, the reaction proceeds the same.

Elemental sulfur was added to the lignite. It may also be added to the alcoholic KHS solution. The total amount of sulfur present was 8.25 grams, which included the organic sulfur content of the lignite.

The apparatus further consists of a container and a conduit for hydrogen or nitrogen as the flushing inert gases (see FIG. 1 herein). These insert gases may be fed directly or are fed through a steam generator via a steam line into the reaction vessel 11. The steam line is heated to 140° C. and enters the reaction vessel near the bottom of the vessel heated at that temperature. Hydrogen sulfide may also be introduced through the steam lines or separately.

Means for measuring temperature are also provided. Typically, the steam line enters through the center opening for the flask. Initially, nitrogen or hydrogen provides the agitation while the methanol of the reagent solution is being distilled. Agitation may be effected by different means as well, such as stirring. The presence of water in the raw lignite produces a methanol (or ethanol) soluble hydrocarbon gas during this distillation.

This liquid hydrocarbon production is minimized when dry lignite is used. The reaction vessel 11 may be of a suitable form, but as used in this experiment, it is a round bottom flask, with appropriate introduction ports at the top thereof.

Another introduction port is for the addition (and removal) of lignite. The reagent is introduced through an appropriate opening which is closed during the run.

A still further port leads to a vertical water cooled condenser which empties into a round condensation flask 14 having an outlet port therefor and a port, at the bottom, for removal of distillates.

Residual gases pass from the condensation flask (vessel) 14 into a second water-cooled condenser 15, conveniently above the same condensation flask 14.

The gases from the condensation flask, i.e., remaining gases, are then passed through a series of scrubbers. The scrubbers consist of at least the following: (a) a water wash, (b) an ethanol (methanol) wash, (c) a one mole solution of KOH in 135 ml of methanol, (d) a benzene wash, (e) a one mole solution of KOH in two moles of water, (f) sulfuric acid wash of about 24% solution of 98% $H_2SO_4$. As a back-fire preventer, an empty scrubber may be used.

The remaining gases thereafter pass through a conduit and are suitably collected by suitable collection means. A chromatograph tube may be inserted before the gas test meter 17 (placed between the scrubbers and the collection means) so that gas samples can be analyzed. A chromatograph tube may also be inserted where desired, in the recovery train and the gases or distillates analyzed.

A gas meter, on this line, calibrated in fractions of a cubic foot, gives a cumulative total of cubic feet of hydrocarbon gas recovered.

In conducting the process, the lignite (and the sulfur it contains) is placed in the reaction vessel and heated to 35°-50° C. 50 ml of reagent are added after flushing the system with helium or nitrogen to expel atmospheric oxygen. The system is closed and the temperature elevated to 65° C., at which temperature the methanol component of the reagent is distilled. As mentioned before, the introduced hydrogen or nitrogen may provide sufficient agitation of the reagent-lignite mixture. The reagent also contains water both as impurities in the ingredients used to make the reagent and additional water is formed as the reagent is formed. The water present in the reagent and coal is distilled off at temperatures up to 135° C.

The distillate produced during the distillation of the methanol (or ethanol) will contain methanol or ethanol soluble hydrocarbon components including gases. Water is distilled from the reaction mass, after most of the methanol has been removed, it is mostly clear. This water may contain a small quantity of amber colored liquid hydrocarbons (which increases with coal rank). At a temperature from 135°-190° C., but typically at 170° to 190° C., a small liquid hydrocarbon fraction will be produced from the reaction mass; again this amount increases with the rank of coal. This liquid hydrocarbon condenses within the water cooled condenser 13, on the walls 13a of the condenser as a solid or semi-solid.

After the water-methanol mixture has bee distilled from the reactant mass, optionally, the introduced helium, hydrogen or nitrogen can be turned off. However, hydrogen sulfide may be introduced instead of sulfur for the reasons further illustrated herein in greater detail. At that point, i.e., at about 170°–190° C. steam is used to agitate the mix or a suitable stirrer may be used. Steam is not introduced into the reaction vessel until the methanol-water mixture has been distilled because the water-methanol mixture will hold the temperature at a specific temperature range during this distillation.

After the introduction of the steam or the steam and continuing hydrogen sulfide introduction, various lignites, and sub-bituminous coals, based on the inherent makeup of these, display different distillation points in the production of sizable amounts of gaseous hydrocarbon.

It is suggested to discontinue the introduction of the inert gases, when steam is injected into the reaction vessel, because an accurate test meter reading of the quantity (volume) of gas emitted from the apparatus cannot be made when the inert gas is being introduced into the apparatus. However, appropriate means such as a second test meter on the hydrogen tank would give an indication of the amount of hydrogen passing into the system and this could be subtracted from the total reading of the final test meter 17.

Generally, for low rank coal a sustained production of hydrocarbon gases begins at the boiling point of methanol or ethanol and continues to increase as the reaction mass is heated to approximately 280° C. For higher rank coal, at these low temperatures, i.e., up to about 280° C. little if any gas production takes place. These gases are mostly taken up in the scrubber system and very low reading is given on the gas meter 17. The above discussion is to be understood as pertaining to the same reagent being used in the reaction, except where specifically noted otherwise.

If the scrubber system is eliminated (and the initial hydrogen sulfide production, from the reaction between the alkanolic reagent and the elemental and organic sulfur—the last in the coal—is separately vented or measured or scrubbed with a suitable aqueous reagent), the gas quantity can be measured.

As previously mentioned, depending on the particular coal, the initial quantity of gas is low, e.g., from lignite at temperatures below 280° C. about 0.025 to 0.05 cu. ft. of gas/50 grams of wet coal is obtained.

Methane is generally given off first and it has a solubility in all of the scrubber system liquids as compared to each of the other recovered hydrocarbons. Pentane, hexane, hexene and pentene also have a considerable solubility in the scrubber liquids used in the system, except in water. Hexenes and hexanes condense in the water cooled condenser and are only gasified further as influenced by the partial pressure of the other lighter gases passing over the liquid. A component of the gas recovered and entering meter 17 is ethene. Ethene has a limited solubility in kerosene and little solubility in the water and alcohol in the various scrubbing stations 16. Ethene has a characteristic smell of unsaturated hydrocarbon while the saturated hydrocarbon gases are odorless. Solubility of unsaturated hydrocarbon gases in sulfuric acid can be used to separate the saturated from the unsaturated hydrocarbons.

When the temperature reaches 335° C., the initial 100 grams of wet lignite or sub-bituminous coal provide a more rapid gas production in the $C_1$ to $C_5$ carbon atom range. The gas production increases substantially when 360° C. is reached and when the final temperature is between 380° C. and 450° C. a very rapid gas production is encountered with some hydrogen being produced. At a temperature of 360° to 380° C. carbonyl sulfide is also produced. In sub-bituminous coal e.g. 4.7% by weight of the total hydrocarbon gas may be carbonyl sulfide. When hydrogen sulfide is used carbonyl sulfide production appears to be suppressed, all other conditions being equal.

At the higher temperature, gases pass the scrubbers and are registered on the flow meter. For example, from 100 grams of wet sub-bituminous coal, after subtracting for hydrogen sulfide, generally up to 1.4 cubic feet of gas from 47 grams of carbon (on dry basis) present in the sub-bituminous coal can be obtained at the higher temperatures.

At standard temperature and pressure, about 3.7 moles of gas containing 47 grams of carbon would indicate an average carbon content of 2.25 for a product. Again, it should be noted that the products produced at different temperature levels consist of different breakdown fractions.

Gas chromatographic analysis of Example 1 run products, gives a strong indication of two hydrogen atoms to each carbon atom in the gases. The initial lignite contained one hydrogen atom for every 1.38 carbon atoms, or, for a direct comparison, 0.725 hydrogen atoms to each carbon atom. Gas chromatographic analysis did not indicate any substantial oxygen present and showed that the collected gases were almost entirely hydrocarbon. The hydrocarbon gases containing from 1 to 6 carbons in that fraction are either gases or very volatile liquids.

The scrubbers do remove carbon dioxide as potassium carbonate as a precipitate in the KOH-ethanol or -methanol solution. Generally, a solution of one mole KOH in two moles of water is used, and the alkanol can be added to this aqueous solution to the alkali metal hydroxide.

EXAMPLE 2

25 grams of industrial grade sodium hydrosulfide flakes were mixed with 100 grams of Maverick sub-bituminous coal. Industrial grade NaHS is in flake form and of varying analysis and this particular sample contained approximately 30% water. These flakes were placed on top of the coal in the reaction vessel. The coal analysis was: moisture 3.3%; ash 12.9%; sulfur 0.69%; carbon 70.2%; hydrogen 4.4%; nitrogen 1.13% and oxygen 6.16% by weight. The heating value for the coal is 12,656 BTU/lb.

The mixture was heated to 280° C. in a reaction vessel. Steam was injected (140° C. steam) at the bottom of the reaction vessel to provide agitation and supply hydrogen for the hydrogenation of the coal. Steam was injected after a temperature of 175° C. was reached. It is believed that the hydrosulfide was decomposed at least partially to the sulfide during this heating as a result of the water content in the reagent and coal.

Below 175° C., a few clear drops of hydrocarbon distilled with the initially expelled water. The reagent bubbles up at 175° C. apparently due to the formation of a lower hydrate of sodium suldfide with the subsequent release of water.

At 280° C. the hydrocarbon gas given off was produced on a continuing basis and a flame could be sustained at the end of the system in the glass tube. The gases were water washed prior to burning. At 350° C. the run was terminated with about half the coal reacted.

The liquid distillate, cooled and condensed in a water cooled condenser was 15 ml and gave an analysis of 9.8% hydrogen, 87% carbon and 0.67% sulfur and 0.07% nitrogen. By chromatographic analysis, the gases were principally ethene. Approximately 0.8 cu. ft. of gas was produced.

EXAMPLE 3

A reagent consisting of 0.24 grams of potassium hydrosulfide per milliliter was mixed with elemental sulfur. 100 ml of the ethanol solution of said potassium hydrosulfide was mixed with 8 grams of elemental sulfur. This elemental sulfur had been added to 50 grams of a lignite containing 44% carbon, 2.68% hydrogen, 33% water, 12% oxygen, 2% nitrogen and 0.5% sulfur. The ash content was 6%.

The coal and the reagent were mixed in a reaction flask and stirred magnetically. The maximum coal particle size was $\frac{1}{4}''$ mesh.

The temperature was raised to 78° C. and then to 95° C. and the ethanol was distilled and condensed through a water-cooled condenser and collected in a condensation flask with a stopcock at the bottom. The ethanol part of the reagent, before the addition of the sulfur was 72-/890×100 or 80.09 ml possible ethanol distillate. 64 ml of the principally ethanol distillate were measured and recovered.

The condensation flask allowed uncondensed gases to pass into a solution of potassium hydroxide in ethanol and through a sodium hydroxide solution in water. From this sodium hydroxide solution the gases passed onto an analytical gas chromatography tube and then into a flow meter and then were vented into a hood.

The process system had been flushed with nitrogen before the run was begun. The hydrogen sulfide evolved in the reaction between the elemental sulfur and the ethanolic potassium hydrosulfide measured 0.25 cu. ft. The hydrogen sulfide was taken up in a potassium hydroxide ethanol solution and the flow meter measurement was of the nitrogen displaced by this evolution of hydrogen sulfide.

Steam was injected into the process-system at 105° C. The steam was generated by boiling 200 ml of water and passing the steam through a tube heated by heating tape into the bottom of the main reaction flask containing the coal and the reagent. The steam was at 140° C. and the reaction flask was at 105° C. and the temperature was decreased to 100° C. After several minutes the temperature began to climb. When the temperature reached 220° C., 0.1 additional cu ft. of flow registered on the flow meter. Between 220° C. and 270° C. an additional 1 cu. ft. of gas flow registered on the flow meter. Between 270° C. and 320° C. an additional 0.8 cu ft. of flow registered on the flow meter. Between 360° C. and 400° C. an additional 2.05 cu ft. of flow registered on the flow meter. Between 360° C. and 400° C., the 6 mm inside diameter tube vented into the hood would sustain a flame when ignited intermittently. This flame could not be blown out but burned a bright blue when blown on.

The run lasted two hours from the time the initial steam was passed into the process system at 105° C. One quarter of the coal remained in the reaction flask at the end of two hours. This one quarter of the coal was carbonaceous material and did not include the ash nor the water content of the initial sample.

Extraction of carbonate material from the potassium and sodium hydroxide washes showed that $5\frac{1}{4}\%$ of the carbon had been used up in the formation of carbonates.

The gas analysis showed a mixture of $C_1$ through $C_6$ saturated and unsaturated hydrocarbons with hydrogen also present.

EXAMPLE 4

100 grams of lignite containing 44% carbon, 33% water, 12% oxygen, 2.8% hydrogen, 1.6% nitrogen, 0.6% sulfur were mixed with 16 grams of elemental sulfur and then contacted with 200 ml. of ethanolic potassium hydrosulfide containing 0.24 grams of potassium hydrosulfide per milliliter.

The gases produced in this example were cooled to ambient temperatures and then passed through a 1 mole of calcium chloride in 225 ml of water and then through $\frac{3}{4}$ mole of ferric chloride in 300 ml of water. The gases were then passed through a gas chromatography collection tube and then through a flow meter. The gases there then passed through a 8 mm inside diameter glass tube and vented into a hood.

The reaction flask containing the lignite and the reagent was heated on a hot plate-stirrer. A glass tube connected the reaction flask with another flask containing 300 ml of boiling water. The connecting tube was wrapped with heating tape to superheat the steam before its introduction into the bottom of the reaction flask.

The system was nitrogen flushed prior to making the run. The flow meter registered 0.25 cu. ft. after the reaction between the elemental sulfur and the potassium hydrosulfide reagent.

The temperature in the reaction flask was elevated to 135° C. to distill off ethanol and reduce the water content of the lignite. At 170° C. a brown-black heavy distillate formed and remained in that part of the water-cooled condenser nearest the reaction flask. The water condensate was amber color and smelled of unsaturated hydrocarbon. Substantial gas formation began at 220° C. and continued through 270° C. The greatest gas formation was at 360° C. to 380° C.

The total gas formation was 10.1 cu. ft. The analyzed gases were saturated and unsaturated hydrocarbons with a corbon content between one and six. Hydrogen was also produced. The vent tube into the hood would sustain a continuous flame. Three and one-half grams of carbonaceous material remained in the reaction flask after 4 hours.

Without being bound to any particular theory, in the practice of this invention, it is believed that oxygen, sulfur and nitrogen are removed from coal by a series of complex reactions made possible by sulfur compounds of potassium or equivalently by the other alkali metal sulfur compounds, as will be explained below. However, it is necessary to exclude atmosphereic oxygen from the process system. The reactions, via the water and hydrogen sulfide molecules, provides hydrogen to react with coal at the point where coal is being deoxygenated, desulfurized or denitrogenated. Hence, for practice of this invention, it is necessary that oxygen be present in coal but the benefit is also gained when sulfur and nitrogen is present in coal in a form such as an organic sulfur or organic nitrogen species. Moreover, higher rank coal, such as bituminous coal, may not as readily be converted to gaseous hydrocarbons although, as explained below, it still may be done when the reaction scheme is appropriately modified.

It has been found that coal with a carbon content below about 70% was almost entirely gasified with no more than 5% being a solid and/or liquid distillate. A coal with about 75% carbon content gave a 10% liquid distillate; the rest was gas. A coal with 82.5% carbon gave 33% liquid distillate; the rest was gas. An anthracite coal of 92% carbon content gave little gas and only about 2% liquid-solid distillate. However, when it was partially oxidized, it can be readily converted into liquid and gaseous reaction products. These conditions obtain when the same reagent is used.

When sodium is used, instead of potassium, about the same amount of liquid distillates are produced, but less gas.

The present invention is concerned preferably with lignite and sub-bituminous coal gasification, but all coals may be gasified or liquid products obtained therefrom. Further, this invention is applicable to sub-lignite and even peat gasification, but economic factors do not render the process as advantageous, due to the lower carbon content in these source materials per equivalent weight. Even wood in chip form may be gassified. Moreover, wood (cellulose, lignite, sugars, etc.) can be converted into gaseous or liquid products.

Potassium is the preferred alkali metal used to form sulfides, hydrosulfides or polysulfides to constitute the reagent of this invention, although the sulfides, hydrosulfides or polysulfides of lithium, sodium, rubidium or cesium can be used.

Sodium hydrosulfide and sodium sulfide are available in commercial quantities. Commercial potassium sulfide better known as "sulfurated potash" is a mixture of potassium thiosulfate and potassium polysulfides. Sulfurated potash displays some ability to convert coals to hydrocarbon but to a lesser degree than does a specifically prepared mixture of potassium hydrosulfide and potassium pentasulfide.

Although rubidium is equally active, for practical reasons, potassium is the preferred hydrosulfide. Sodium is also useful as sodium hydrosulfide and polysulfides do undergo the necessary reactions. Cesium, rubidium, potassium and sodium, hydrosulfides, sulfides and polysulfides are useful but cesium and rubidium are not cost advantageous. Lithium may also be used, but is less effective than sodium. A mixture of rubidium, potassium and sodium sulfides (generic), may be used with greater effectiveness than any of the individual (generic) sulfides. The term "generic" is intended to mean the series of sulfides beginning with hydrosulfides to polysulfides. The preferred ratio is 14% rubidium, 26% potassium and 60% sodium sulfides (generic) by weight of the elemental metal. The ratio ranges for the preceding mixture are 1:1.5-2.5:3.5-4.5, respectively.

A preferred admixture of potassium hydrosulfide and potassium pentasulfide may be prepared by dissolving 1 mole of potassium hydroxide in 140 ml of methanol, 200 ml of ethanol or 333 ml of 1-propanol or increasing quantities of higher straight chain hydrocarbon alcohols. To this solution, hydrogen sulfide is added to saturation. Sufficient water must be present to prevent the formation and precipitation of potassium sulfide. Potassium sulfide is only slightly soluble in alkanols. On a mole basis, the total water content, including the water impurity in the alkanol and in the particular potassium hydroxide used, is nine milliliters of per mole of potassium hydroxide dissolved in 140 milliliters of methanol, 18.5 milliliters of water per mole of potassium hydroxide dissolved in 200 milliliters of ethanol. Due to the progressive decrease of solubility in higher alkanols of potassium sulfide, progressively greater quantities of water must be added to form potassium hydrosulfide with hydrogen sulfide. Potassium hydrosulfide is not stable in the presence of the increased water content of the potassium hydroxide solutions in alkanols higher than ethanol. The potassium sulfide formed will reduce the hydrogen sulfide and form a red layer of potassium polysulfide, of unknown sulfur content. The precipitated potassium polysulfide can be used as the reagent for the process of this invention when elemental sulfur is added to form known empirical sulfur value polysulfides.

The amount of potassium hydrosulfide of coal is from 5 to 30 grams per 100 grams of coal with about 10 to 25 grams being normally employed. Typically, about 18 grams of potassium hydrosulfide per 100 grams of coal is used. However, as will be further explained herein, this reagent is reconstituted. If potassium in coal ash is converted to hydrosulfide, no loss of potassium hydrosulfide is experienced; and the reagent balance for the reaction, on batch or continuous basis, is very favorable. Moreover, with hydrogen sulfide stabilization of the reagent, the amount of reagent used may be decreased.

In general, it is emphasized that sufficient amounts of sulfur, sulfide, hydrosulfide or polysulfide should be present to take up the sulfur expelled from the reagent from oxygen in coal during deoxygenation thereby preventing the expelled sulfur from dehydrogenating the coal at a temperature above 175° C. Also, the integrity of the various reagent species must be preserved above 325° C. since a temperature increase above this level will cause a slow dehydrogenation of coal by alkali metal hydroxide melt. As sulfur causes the formation of polysulfides and the alkali polysulfide is less hydrolyzed with increasing sulfur content thereof, the decomposition by steam (or other water) of the hydrolysis product, i.e., the hydrosulfide is thereby prevented; however, hydrogen sulfide addition accomplishes best the stabilization as further explained herein.

The amount of elemental sulfur to be added to the alkanol solution of potassium hydrosulfide is one atom of sulfur for each oxygen, sulfur and nitrogen atom present in the coal to be treated. The amount of potassium hydrosulfide to be used is at least twice that required to react with this determined amount of sulfur according to:

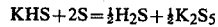

If sodium hydrosulfide is used as the reagent the reaction with elemental sulfur is:

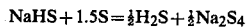

At temperatures above 175° C., the sulfur displaced by oxygen will de-hydrogenate the coal. It is necessary to use twice the amount of sodium or potassium hydrosulfide as that used initially to react with the elemental sulfur addition in the reagent preparation.

As measured by alkaline earth carbonate formation, the carbon lost to the production of carbon dioxide did not exceed 6½% of the total carbon present.

The hydrogen sulfide generated in the addition of the elemental sulfur to the alkanolic solution of alkali metal hydrosulfide and the reaction of the sulfur displaced by oxygen during the conversion of coal to hydrocarbon forms is used to form additional alkali metal hydrosulfide from the alkali metal hydroxide form recycled from the process or is reintroduced into the reactor(s) to stabilize the reagent as will be explained.

Some of the potassium hydrosulfide is decomposed following hydrolysis into potassium hydroxide and hydrogen sulfide. This potassium hydroxide provides a medium at temperatures of 360° C. and higher whereby the calcium carbonate of the limestone of the ash content of the coal reacts with the potassium sulfate of the residue to form calcium sulfide and a mixture of potassium hydroxide and potassium carbonate. The potassium content of the coal ash is also extracted into hydroxide form at this time.

A selection of the necessary amount of reagent is fairly certain for each type of coal and can be readily established for that coal based on the above broad ranges for the reactants and the amounts of sulfur present in coal.

In calculating sulfur in coal, only organic sulfur, i.e., sulfur bound to carbon, is taken into consideration. Nitrogen in coal is converted to ammonia and, for a large scale operation, may be recovered as a valuable by-product.

Steam as shown above is employed at a temperature at which the reaction is sought to be conducted, i.e., depending on the type of coal and the decompsoition levels of coal as well as the desired product. Steam also provides a source of hydrogen apparently as $H^+$ (apparently not from $OH^-$).

As a general rule, most coals require six to seven moles of water generated into steam per three and one-half moles of carbon present in coal.

Appropriate steam generation at the selected temperature may be in the generator 12 shown in the FIG. 1. As a suitable amount, sufficient steam is used, e.g., to provide hydrogen for hydrogenation of coal having a hydrocarbon end product from one to two carbon atoms. If less hydrogenation is sought, less steam is used.

As the amount of sulfur content of the reagent is increased, i.e., from sulfur in coal and added elemental sulfur, the reaction temperature is lowered. For example, a reaction temperature of 380° C. is lowered to 350° C., when, as an illustration, the sulfur balance is representative of a theoretical compound $K_2S_3$ producd and maintained during reaction conditions. A corollary of this phenomenon is that larger molecules are produced, for example, pentane, i.e., isopentane and pentane.

Further, rank of coal affects the distillate makeup, the higher the rank of coal, the higher the proportion of liquid distillates under equivalent conditions, e.g., when using the theoretical $K_2S_3$ compound at the same temperature conditions.

Of course, as mentioned before, when the temperature is varied, the product composition changes. Moreover, as illustrated above, when the amount of sulfur in the reagent is changed, the product composition is also changed.

Thus, based on the above, one can vary temperature, sulfur content of reagent, employment of mixtures of reagents, e.g. liquid or dissolved forms thereof, rank of coal, and use a recycle of alcohol absorbed distillates (as further explained herein) to obtain the desired product cut. Within variation of a product cut, recycle is contemplated of various other distillates in the recovery train shown in the FIG. 1 herein.

The above described variations are within the following prescription: temperature up to 425° C. to 450° C. but distillation starts at 40° to 50° C.; sulfur content in reagent (e.g., for potassium) $K_2S$ but the sulfur content may go up to $K_2S_5$; sulfur or hydrogen sulfide addition; mixtures of these reagents; liquid or solid state of reagents; contacting of a product stream with another composition of reagents, including hydrogen sulfide; and rank of coal is desirably in the lignite to bituminous coal range. When applied to anthracite, the results are less advantageous although a distillate may be obtained at +380° C. and using a reagent such as $K_2S_4$. Partial oxidation of the high rank coal also helps.

For sodium, the useful sulfur species are NaHS, and the $Na_2S$ to $Na_2S_2$ sulfides; NaHS is more stable than KHS with respect to water in coal or steam and starts reacting to produce a distillate at temperatures correspondingly lower (about 10° to 20° C. lower) from that of potassium, although in somewhat lesser amounts that potassium. Rubidium, while not price advantageous, is at least as good and often even better than potassium.

If the alcoholic distillate (including any hydrocarbon components present) is recycled from separator 14 depicted in the FIG. 1 herein to the reaction vessel 11, the product composition may also be varied. Moreover, the amount of recycle may also be varied. Thus, up to about 280° C., the product composition can be forced towards a composition which is a liquid distillate of a boiling point below about 180° C. At a reaction temperature up to about 310° C. paraffin distillates are formed when employing the above-described alcohol recycle to the reaction vessel. As before, and in this recycle condition, water, i.e., steam at a temperature of about 135° C. and higher must be present in order for the reaction to occur; advantageous is also hydrogen sulfide addition.

For the alcohol recycle, methanol is the preferred alkanol. As can be seen from this aspect of the recycling, the alcoholic distillate provides for a further product modification employing the alcohol dissolved initial reaction products in the reaction vessel. As a result of this aspect, more liquid distillates may be obtained.

When starting the process at about ambient conditions (and raising the temperature), elemental sulfur or preferrably hydrogen sulfide is added to coal or to the reagent to obtain the selected sulfur content for the reagent. At these conditions $H_2S$ formed in the system during the reaction of the sulfur and the reagent is removed from the gas stream and wash system to reconstitute the reagent as shown in FIG. 2. As the temperature is being brought up, when steam is not used, any hydrogenation of coal that occurs is from the water content in coal or the reagent. At about 135° C., steam may be added if light distillates are desired. Typically, steam is added, however, at about the temperature when a hydrate of the reagent starts reforming or reconstitutes itself to a lower hydrate thereof. For potassium based reagent, steam addition temperature is selected at about 170° C.

As the precursor hydrates rearrange to lower hydrates and give up water of hydration, copious amounts of steam are liberated. Thus, that condition signals the point at which steam may be safely introduced, provided the water of hydration has left the reaction vessel.

The process can also be carroued out continously. Generally, a particular temperature level is selected and coal and reagent is introduced in the reaction zone, ashes withdrawn and the reagent and alkali metal part of the reagent recovered therefrom and the reagent reconstituted, e.g., with hydrogen sulfide. The liquid and gaseous fractions are recovered typically in a distillation column or appropriate scrubbers including the hydrogen sulfide. Consequently, a fully continuous process with a reagent reconstitution—recycle is possible based on the illustrations shown herein producing a desired cut of product for the preselected temperature and other operating conditions.

In outlining the complex stages by which the reactions are believed to proceed, it must be remembered that the present understanding is derived by inference as many reactions are simultaneously taking place. Hence, the following explanation is only offered in aid of understanding and not in any way to espouse the correctness of a particular reaction or a theory because this invention can be understood and practiced without reference to any theory.

It is also known that sulfur, in elemental form, will dehydrogenate coal at temperatures in excess of 175° C. (Mazumdar et al., Fuel, Volume 41, pp. 121 et seq., (1962)). Further, air oxidation of potassium pentasulfide produces elemental sulfur, potassium thiosulfate ($K_2S_2O_3$) and potassium tetrathionate ($K_2S_4O_6$). (Letoffe et al., Journal Chimie Physique, Vol. 71, pp. 427-430 (1974)). Potassium pentasulfide decomposes into potassium tetrasulfide and sulfur at 300°—this reaction is a slow reaction which progressively increases as the temperature is elevated above 300° C.

Potassium sulfide will hold 5 molecules of water of hydration up to 150° C. when it becomes the dihydrate; and the dihydrate is decomposed, at 270° C., to a solid lower hydrate and water and a still lower hydrate to 779° C. to 840° C. at which temperature potassium sulfide decomposes to the disulfide and elemental potassium. Elemental potassium is soluble in the solid sulfide. The thiosulfate ($K_2S_2O_3$) is decomposed above 200° C. to the sulfate plus the pentasulfide and the pentasulfide is, in turn, decomposed to the tetrasulfide and sulfur at temperatures beginning at 300° C.

When the potassium hydrosulfide (in alkanol) is used as the reagent, the water content of the coal and the water present in the solution of the potassium hydrosulfide react to cause hydrolysis and then decomposition to hydrogen sulfide and potassium hydroxide. Potassium hydroxide will react with nondecomposed potassium hydrosulfide to form potassium sulfide (in hydrated form) and water. Potassium pentasulfide (formed by the reaction with the organic sulfur of the coal and the added elemental sulfur) form potassium hydrosulfide as follows:

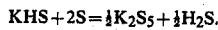

$$KHS + 2S = \tfrac{1}{2}K_2S_5 + \tfrac{1}{2}H_2S.$$

For sodium the reaction is:
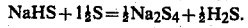
$$NaHS + 1\tfrac{1}{2}S = \tfrac{1}{2}Na_2S_4 + \tfrac{1}{2}H_2S.$$

No intermediate sulfur content polysulfides (defined as sulfides with 2 to 5 sulfur atoms) are formed in the reaction with potassium and insufficincy of sulfur will leave unreacted KHS. However, this reaction only occurs in alkaholic solutions. For sodium species only the tetrasulfide species is formed.

Potassium sulfides with a sulfur content less than that of the pentasulfide are decomposed by oxygen to potassium thiosulfate.

In summary, as oxygen is removed as well as nitrogen and organic sulfur, water or hydrogen sulfide (continually produced by contact between water and the reagents) yield hydrogen to the coal at the point where coal has been deoxygenated, desulfurized, or denitrogenated; nitrogen comes off principally as ammonia; the sulfur comes off to form an alkali (e.g. potassium) polysulfide and at lower temperatures forms a mercaptan with the alkanol solvent. Mercaptans are absorbed in alcohol and in the KOH-alcohol solution. This overall reaction proceeds through reduction of the hydrogen sulfide gas to sulfur and water, with subsequent reaction of the sulfur with the KOH to form the potassium thiosulfate and the potassium sulfide as shown above. The potassium sulfide can then acquire additional sulfur from hydrogen sulfide to form potassium polysulfide and are the reagents used in the reaction.

In general, at different temperature levels, the coal breakdown products have different compositional makeup. These temperature levels can be selected for the desired compositional makeup for the volatile distillates and gaseous fractions suitable for a particular end use. For example, at a temperature between 340° C. and 365° C., the following gas analysis was obtained for a product gas obtained from a sub-bituminous coal: methane 80.19%; ethane 1.41%; propane 2.67%; propene 1.41%; iso-butane 0.16%; n-butane 0.31%; hydrogen sulfide 0.001% and carbonyl sulfide 4.72% residue was apparently ethanol.

The above described compositions i.e., gaseous fractions, obtained at different temperature levels, may be further treated such as in another reactor with other reagent composition, that is, one higher in sulfur content and at a lower temperature from that in the first stage where the reaction temperature is 340° C. to 390° C., in the next stage the temperature may be 280° C. to 340° C. with increasing sulfur content in the reagent; in the third stage, the temperature may be 225° C. to 280° C. or 180° C. to 225° C. As the dehydrogenation reaction is in competition with hydrogenation reaction with increasing sulfur content in reagent and the presence of sulfur causes dehydrogenation the product stream initially gaseous can then be treated to obtain the desired degree of mass i.e., API Number for a preselected product. In other words the initial gaseous products are reformed into products as dictated by the demand.

As mentioned before, the above process has been improved by the addition of hydrogen sulfide to the reagent during the coal or coal product hydrogenation stage, i.e., the alkali metal sulfides, mixtures of sulfides such as in their hydrated form etc. The hydrogen sulfide addition, apparently, keeps the selected reagent in a stable state so that a reaction once initiated with that particular reagent or reagent mixture will produce, with few variations, from the same source material, when keeping all other conditions constant, substantially the same products or mixtures of products. Consequently, proper stagewise arrangement of reagents, their compositions for each of the stages, temperature conditions and water addition will be further improved by the hydrogen sulfide addition to the above described process so that a greater range of products, selected product mixture and a more precise degree of hydrogenation (including dehydrogenation of a product stream(s), when desired), are now possible.

Thus, the appropriate alkali metal sulfides, mixtures of the sulfides, and mixtures of the foregoing sulfide(s) hydrates provide the desired reagent stability, and thus selected product, when properly maintained in the "active" reagent state by the addition of hydrogen sulfide.

The reasons for the hydrogen sulfide addition follow from the illustrated reactions.

$$4KOH + 4H_2S \rightarrow 4KHS + 4H_2O \quad (1)$$

When coal derived sulfur is present then $$4S + 6KOH \rightarrow K_2S_2O_3 + 2K_2S + 3H_2O \quad (2)$$

in turn $$K_2S_2O_3 + 3H_2S \rightarrow K_2S_5 + 3H_2O \quad (3)$$

the decomposition of $K_2S_2$ is as follows:

$$4K_2S_2 + 8H_2O \rightarrow 4KOH + 4KHS + 4S + 4H_2O \quad (4)$$

Hence, if $H_2S$ is present, KOH is converted to KHS and if any KOH forms the thiosulfate, then the thiosulfate is converted to $K_2S_5$.

Further reactions are as follows:

$$K_2S_5 \rightarrow K_2S_4 + S \text{ (above } 300° \text{ C.)} \quad (5)$$

$$K_2S_4 \rightarrow K_2S_3 + S \text{ (above } 460° \text{ C.)} \quad (6)$$

$$KHS + K_2S + 3H_2O \rightarrow 3KOH + 2H_2S \quad (7)$$

$$K_2S + H_2O \rightarrow KOH + KHS \quad (8)$$

$$KHS + H_2O \rightarrow H_2S + KOH \quad (9)$$

$$KHS + KOH \rightarrow K_2S \cdot xH_2O \quad (10)$$

(x can be, e.g., 2, 5, etc., depending on temperature). Hence, enough $H_2S$ should be present to keep the reactions, by mass action, in a state, where the reagent is stable, i.e., sulfur is taken up either when freed from coal or from the reagent, and hydrogen sulfide keeps the reagent from hydrolyzing. Moreover, the thiosulfate generated by the oxygen present in coal is regenerated during the reaction to the desired $K_2S_5$ sulfate. Thus, the reagent is kept in the desired hydrolysis level by $H_2S$.

Of the various reagents, the following are preferred because of stability and sulfur acquisition ability, KHS, NaHS, $K_2S$, $K_2S_2$, $K_2S_3$; and of these, the order of preference is as follows: $K_2S_2$, $K_2S$ and then $K_2S_3$. The other sulfides display instability at their melting points, e.g., $Na_2S_2$ at 445° C., $Na_2S_4$ at 275° C.; or give off sulfur at 760 mm, e.g., $K_2S_5$ at 300° C. yields $K_2S_4 + S$; $K_2S_4$ at 460° C. yields $K_2S_3 + S$; and $K_2S_3$ yields $K_2S_2 + S$ at 780° C.

Melting points of the alkali sulfides illustrated above are as follows: for $K_2S$ at 948° C.; $K_2S_2$ at 470° C.; $K_2S_3$ at 279° C. (solidification point); $K_2S_4$ at 145° C.; $K_2S_5$ at 206° C.; $K_2S_6$ at 190° C. Melting points for mixtures of the sulfides (pure or eutectic mixtures) are as follows: for $K_2S$-$K_2S_2$ it is 350° C.; for $K_2S_2$-$K_2S_3$ it is 225° C.; for $K_2S_3$-$K_2S_4$ it is about 110° C.; for $K_2S_4$-$K_2S_5$ it is 183° C. Based on the various illustrations above, appropriate temperature conditions are selected as dictated by decomposition and/or melting point characteristics so as to allow the use of a solid reagent, or a stable liquid reagent. Of course, the various hydrates of the alkali sulfides have various melting and/or decomposition points which, of course, also holds true for the eutectic mixtures. These temperature points may be readily established thermographically as it is well known to those skilled in the art.

Hence, at peak operating temperature herein, e.g., 450° C., $K_2S_5$ will yield sulfur, (which is a useful phenomenon as has been explained herein in connection with dehydrogenation of further process streams). Inasmuch as the decomposition temperatures are lowered at lower pressures, the coal conversion at atmospheric pressure is entirely feasible, although some benefit is gained by operating at elevated pressures, e.g. above 5 atm., the added cost and other expenditures make this merely a less desired method of operating the coal conversion process. Hence, for practical purposes the variation of the pressure conditions can be from about ½ atmosphere to about 5 atmospheres, but the ambient atmospheric pressure is preferred. In describing the various sulfides and their decomposition temperatures including the reactions, my U.S. Pat. No. 4,210,526 issued July 1, 1980 is relevant and for this reason is incorporated herein by reference.

The coal conversion process proceeds without a reagent instability, i.e., sulfide hydrate instability, because hydrogenation of coal is preferrential to reagent decomposition and addition of hydrogen sulfide aids in the stabilization of the reagent. Moreover, while the reaction with coal will proceed with adequate amount of reagent present, the addition of hydrogen sulfide also decreases the amount of the reagent necessary because the reagent is in a more stable form, hence, the process is also improved on that basis. The use of hydrogen sulfide doubles at least the product recovery, all other conditions being the same.

In general, the hydrogen sulfide addition will be on a space time velocity basis and will be typically in a range from 40 to 120 ml/min/gal (about 10 ml/min/liter to 30 ml/min/liter) of reactor space with about 20 ml/min/liter being typical. Expressed on another basis, one half gram mole, and less of $H_2S$ is added for 1000 ml of water removed by the hydrogenation reaction.

Although the reaction mass of coal and reagent may be appropriately stirred, it is best to precoat coal with a reagent in the absence of oxygen, as oxygen has a tendency to destroy the reagent.

For this reason, it has also been found useful to employ a liquid or a dissolved reagent. Liquid, yet stable reagents may be employed for coating coal at or above the appropriate melting point of the selected reagent or the liquid eutectic mixture of these.

For example, a mixture of $K_2S_3$-$K_2S_4$ may be used above 110° C. in a liquid state to coat coal. As solvent for the above reagent, glycerol has been found to be very useful. Any solvent which will dissolve the sulfides and will not affect their activity may be employed. About 88 grams of KHS is solubilized to make a total of 200 ml glycerol solution. When the mixture is heated up to 175° C. (glycerol will decompose above 190° C.), $H_2O$ is driven off from the dissolved KHS mixture and the mixture will then contain $K_2S \cdot xH_2O$. Oxygen is excluded also from this reaction mixture. This mixture can then be readily used for coating coal and thus serve as a reagent.

Inasmuch as the severity of the attack on sulfur, nitrogen and oxygen on coal is a function of the reactant composition and the amount thereof, the following points may be mentioned. Gaseous conversion of coal is accomplished when degradation, of coal, i.e., reagent attack thereon is most severe. Less severe degradation produces lighter distillates. At 175° C., sulfur starts to dehydrogenate coal and therefor presence of sulfur is not desired for coal conversion. Hence, a stable reagent is employed at those conditions. However, for reformation, i.e., dehydrogenation and reaction of dehydrogenated species with each other, that reaction is important as it allows preselected obtention of liquids of different boiling points (or preselected API number). Of course, coal derived gases are an ideal feedstock for reforming hydrocarbons. As mentioned above, the rank of coal also affects the reactions. For poorer coal, to achieve least degradation high sulfur content reagents are used. For more complete gassification, the amount of sulfur in the reagent is decreased, e.g., $K_2S$ is used, whereas $K_2S_5$ is used for less severe attack. This is especially true for peat when it was reacted with $K_2S_5$, it gave essentially naphthalene. The above will now be further illustrated by the following examples.

EXAMPLE 5

A reaction vessel of, 1 gallon capacity, is equipped with a steam line, a heating-cooling means, a thermocouple, stirrer, and an exit conduit for the reaction gases. Hydrogen sulfide is added with steam and it may also be added separately. The products are recovered in a condenser appropriately cooled while the gases are collected as previously illustrated in the Figures herein.

To 800 grams of Kentucky #9 coal held under a helium gas blanket, in the described vessel, was added a liquid mixture of $K_2S_3$ and $K_2S.5H_2O$. The added amount of the reagent mixture was 2 moles, i.e., one mole of each. One mole was $K_2S_3$ obtained from a mixture of $K_2S$ and $K_2S_5$ in a water solution adjusted to an empirical formula $K_2S_3$. Further, 4 grams of KOH was added, which serves to drive off $NH_3$ at process conditions. The mixture was stirred so as to coat the coal particles with the reagent.

After this, steam was added together with $H_2S$ at 80 ml/min at a temperature of 50° C. The reaction was exothermic and was not allowed to rise above 450° C. but kept as much as possible at about 350° C. to 390° C. Steam was added at 135° C. at a rate equivalent to hydrocarbon withdrawal or at 130% thereof, the recovered product was a clear amber red solution, which, when treated under same conditions with 19 gr of KHS, up to 240° C., completely distilled to a water clear hydrocarbon liquid distillate almost water clear hydrocarbon and of a water like viscosity. A total of 324 ml of distillate was recovered including 12 liters (N.T.P.) of gas during the first reaction stage. The product analyzed as follows:

| Boiling Point Range |
| --- |
| 180° F. initial boiling point and |
| 10%–460° F. |
| 20%–479° F. |
| 30%–486° F. |
| 40%–492° F. |
| 50%–500° F. |
| 60%–508° F. |
| 70%–522° F. |
| 80%–538° F. |
| 90%–562° F. |
| 95%–592° F. |
| 98.6%–632° F. |
| (1.4% Residue — heavy liquid) |

EXAMPLE 6

In order to illustrate the efficacy of $H_2S$ addition, 110 grams of bituminous coal (on a dry ashless basis), was reacted with solid NaHS (technical grade), or KHS (in water solution), in a reaction vessel as previously described, with addition of $H_2S$ at 80 ml/min and 200 ml helium. Steam was added at a temperature above 137° C. at a rate from equal to 130% of hydrocarbon condensate removal. Addition of KOH, suppresses ammonia reactions within reactor and expells ammonia. The reaction becomes exothermic at 390° C. 252 liters of gas and 70 ml of liquid hydrocarbon comdensate was obtained before the reaction run off exothermically above 390° C.

When runs were made on lignite with and without $H_2S$ addition, the yields were more than doubled for the run with $H_2S$ addition. The reagent was as illustrated in Example 6. The reaction also became exothermic above 390° C.

About 3 moles of $H_2S$ per mole of $K_2S_2O_3$ formed is necessary. Further, about 48 grams of coal based oxygen is used up when one mole of $K_2S_2O_3$ is formed. About 42% of wood is oxygen and about 2% of anthracite is oxygen. Between these limits $H_2S$ is added based on the above reaction as a maximum, as there are other conpeting reactions. The above is a rough indication of the amount of $H_2S$ needed but in practice lesser amounts, e.g. due to the principal side reaction of diatomic hydrogen uniting with oxygen to form water.

When KHS and/or NaHS are used these produce copious amounts of gas, and the reaction becomes exothermic above 390° C. $K_2S.5H_2O$ plus $K_2S$ (empirical, based on equal molar quantities of $K_2S.5H_2O$ and $K_2S_3$) produces little gas and considerable amounts of liquid condensate, from the same source material, but the reaction is exothermic from inception, i.e. about 50° C. and the reaction seams to maintain itself at 390° C. with little heat input. $K_2S_2$ (derived from a melt of $K_2S.5H_2O$ plus sulfur) mixed with an equal quantity of $K_2S$ (derived from hot KOH aqueous solution plus sulfur in a ratio of $6KOH+4S$) as a reagent, produces liquid distillate and gas. Reaction becomes exothermic at 240° C. when used on the same source material. In all three instances the source material was −200 mesh Kentucky No. 9 bituminous coal and the reaction condition were otherwise identical, i.e. steam, $H_2S$, and helium were used as previously illustrated. The foregoing shows the possibilities of obtaining gas, gas and distillates, and substantially distillates, and moreover, shows the highly advantageous nature of the exothermic reactions. In these exothermic reactions negligible amounts of CO and $CO_2$ were formed. In the gas streams, after scrubbing, hydrogen sulfide was nondetectable. Apparently no COS was formed.

It has been demonstrated above, that a readily available source of a great variety of hydrocarbons may be realized from coal by a very flexible process carried out at low temperature, low pressure while reconstituting the reagent, as part of the process.

What is claimed is:

1. A process for conversion of coal to gaseous hydrocarbons and volatile distillates comprising the steps of:
reacting coal or peat and a hydrosulfide, a sulfide or a polysulfide of an alkali metal, hydrates thereof, or mixtures thereof in presence of water, wherein water is added during the reaction, at a rate sufficient to hydrogenate the coal or peat to obtain the desired end product cut of gas or liquid or mixtures of both, adding sulfur or hydrogen sulfide or neither, said hydrogen sulfide being added, on space time velocity basis, from about 10 to about 30 ml/min/liter, said reaction being at a temperature between 50° C. and up to 450° C. at a pressure from subatmospheric to about 5 atm., and recovering volatile liquid distillates and hydrocarbon gases as hydrocarbon values.

2. A process for conversion of coal to gaseous hydrocarbons and volatile distillates comprising the steps of:
reacting coal or peat and a hydrosulfide, a sulfide or a polysulfide of an alkali metal, hydrates thereof, or mixtures thereof in presence of water, wherein water is present during the reaction, at a rate equivalent to about the amount of hydrocarbon recovered to about 130% of the hydrocarbon recovered, adding sulfur or hydrogen sulfide or neither, said hydrogen sulfide being added, on space time velocity basis, from about 10 to about 30 ml/min/liter, said reaction being at a temperature between 50° C. and up to 450° C. at a pressure from subatmospheric to about 5 atm., and recovering volatile liquid distillates and hydrocarbon gases as hydrocarbon values.

3. A process for conversion of coal to gaseous hydrocarbons and volatile distillates comprising the steps of:
reacting coal or peat and an alkali metal hydrosulfide, a sulfide, a polysulfide, hydrates thereof, or mixtures thereof, at a temperature of 50° C. and above, at a pressure from subatmospheric to about 5 atm., in the presence of water, such that the amount of water used is from about six to about seven moles per three moles of carbon in said coal, or in the presence of water and hydrogen sulfide, said hydrogen sulfide being added, on a space time velocity basis, from about 10 to about 30 ml/min/liter, continuing said reaction at a temperature up to about 425° C. and recovering volatile liquid distillates and hydrocarbon gases as hydrocarbon values.

4. The process as defined in claim 3, wherein elemental sulfur is added to an alkanolic solution of said alkali metal hydrosulfide used as a reagent.

5. The process as defined in claim 3, wherein said alkali metal hydrosulfide is potassium hydrosulfide.

6. The process as defined in claim 3, wherein said alkali metal hydrosulfide is sodium hydrosulfide.

7. The process as defined in claim 3, wherein said alkali metal sulfide is a mixture of rubidium, potassium, and sodium hydrosulfides and sulfides.

8. A process for conversion of coal to gaseous hydrocarbons and volatile distillates comprising the steps:
reacting coal or peat having oxygen, sulfur or nitrogen present in bound form with an alkali metal hydrosulfide, sulfide or polysulfide or mixtures of same or of mixed alkali metals thereof, as a reagent;
said reaction being conducted at a pressure from subatmospheric to about 5 atm. between the temperatures of 50° C. to 450° C. in presence of water or steam or steam and hydrogen sulfide, said water or steam being added being in relationship to the amount of hydrocarbon recovered and being from about the amount equivalent to about 130% in excess of the amount of hydrocarbon values recovered;
recovering volatile distillates or gaseous hydrocarbons as hydrocarbon values, and
reconstituting said reagent.

9. The process as defined in claim 8, wherein hydrogen sulfide is recovered.

10. The process as defined in claim 8, wherein the coal is lignite coal.

11. The process as defined in claim 8, wherein the coal is sub-lignite.

12. The process as defined in claim 8, wherein the coal is bituminous or sub-bituminous coal.

13. The process as defined in claim 8, wherein peat is reacted.

14. The process as defined in claim 8, wherein the alkali metal is potassium.

15. The process as defined in claim 8, wherein the hydrosulfide, sulfide, or polysulfide is of an alkali metal mixture of rubidium, potassium, and sodium.

16. The process as defined in claim 8, wherein the alkali metal is sodium.

17. The process as defined in claim 8, wherein part of the distillate is returned as an alcoholic solution to take part in the reaction of coal or peat and said reagent.

18. The process as defined in claim 8, wherein the reaction is conducted at a temperature between 135° C. and 450° C.

19. The process as defined in claim 17, wherein the reaction is conducted at a temperature between 170° C. and 380° C.

20. A continuous process for conversion of carbonaceous values in coal or peat and the like to gaseous hydrocarbons and volatile distillates comprising the steps of:
introducing continuously into a reaction zone, maintained above 50° C. and up to 450° C., at a pressure from subatmospheric to about 5 atm., said carbonaceous values as coal or peat;
introducing continuously, as a reagent, a hydrosulfide, a sulfide or polysulfide of an alkali metal or hydrates thereof, a mixture of alkali metal sulfides, or mixtures of hydrosulfides, sulfides and polysulfides thereof as said reagent;
introducing water or steam in said reaction zone for hydrogenation of coal or peat at a temperature between 160° C. and up to 450° C. at a rate dependent upon the preselected end product cut desired;
reacting continuously said carbonaceous values in coal or peat and said reagent in said zone at a predetermined temperature in the presence of said introduced water or steam to hydrogenate said carbonaceous values;
recovering volatile and/or gaseous products from said reaction zone as hydrocarbon values;
recovering hydrogen sulfide or carbonyl sulfide from said reaction zone;
recovering residues including coal or peat ash from said reaction zone;
recovering unreacted reagent or converting residues from said coal or peat including alkali metal values as alkali metal hydroxide from said residues;
reacting said alkali metal hydroxides with hydrogen sulfide given off during said reaction and reconstituting said reagent, and
introducing a sufficient amount of said reconstituted reagent in said reaction zone so as to continue said hydrogenation reaction of said carbonaceous material and said reagent.

21. The process as defined in claim 20, wherein said carbonaceous material is wood.

22. The process as defined in claim 20, wherein the reaction zone is maintained at a set, predetermined temperature for production of gaseous hydrocarbons.

23. The process as defined in claim 20, wherein the reaction zone is maintained at a temperature suitable for recovery of a predetermined hydrocarbon cut.

24. The process as defined in claim 20, wherein an alcohol solution containing a portion of said dissolved distillate is recycled to said reaction zone.

25. The process as defined in claim 20, wherein lignite coal is the coal being reacted.

26. The process as defined in claim 20, wherein potassium sulfide, potassium polysulfide, potassium hydrosulfide or a mixture of same is used as a reagent.

27. The process as defined in claim 20, wherein the temperature in said reaction zone is between 135° C. to 450° C.

28. The process as defined in claim 20, wherein the temperature in said reaction zone is in stages between 170° C. to 450° C.

29. The process as defined in claim 20, wherein a mixture of rubidium, potassium, and sodium polysulfides, sulfides, hydrosulfides, or mixtures thereof is used as the reagent.

30. The process as defined in claim 20, wherein industrial sodium hydrosulfide as the reagent.

31. The process as defined in claim 20, wherein the reagent is resonstituted by reacting an alkali metal hydroxide in a saturated alcoholic solution with hydrogen sulfide, precipitating said reagent as a mixture of a sulfide and hydrosulfide of said alkali metal and recovering said precipitate as a reagent for reacting the same with said coal or peat or gaseous products thereof.

32. The process as defined in claim 20, wherein sad hydrocarbon products are distilled for recovery of a desired product cut.

33. The process as defined in claim 20, wherein said hydrocarbon product, in liquid or gaseous form, is treated in separate stages with said alkali reagent with increasing sulfur content of said reagent at discrete and decreasing temperature ranges below 400° C. but at a temperature above 100° C.

34. The process as defined in claim 33, wherein the gaseous hydrocarbon is scrubbed in an alkali metal hydroxide solution thereby removing hydrogen sulfide from said gaseous hydrocarbon as a reaction product with said alkali metal and further recovering said reagent for recycle of same.

35. The process as defined in claim 20, wherein, as said reagent there is used a theoretical composition $K_2S_3$, on basis of material balance.

36. The process as defined in claim 20, wherein anthracite coal or oxidized anthracite coal is reacted with said reagent.

37. A process for converting coal to hydrocarbon distillates, comprising contacting said coal with a reagent comprising of alkali metal sulfides, hydrosulfides, polysulfides, hydrates thereof or mixtures thereof, heating the resulting system to above 100° C., at ambient pressure, passing steam through said system in the absence of extrinsic air at temperatures between 100° C. and 450° C., recovering a hydrocarbon distillate consisting of both saturated and unsaturated hydrocarbons having a carbon content between one and six and hydrogen and leaving behind an inorganic residue.

38. The process of claim 37, comprising using potassium hydrosulfide and potassium pentasulfide, said hydrosulfide being present in at least a stoichiometrically equal amount to said potassium pentasulfide, the sulfur content of said potassium pentasulfide being above that of the monosulfide ion and at least numerically equal on an atom number basis to the total number of oxygen, sulfur and nitrogen atoms present in said coal.

39. The process of claim 37, wherein the alkali metal sulfide is potassium sulfide and the alkali metal polysulfide is potassium pentasulfide and wherein the number of sulfur atoms in the potassium pentasulfide above that of the potassium monosulfide ion is at least numerically equal to the number of atoms of oxygen, sulfur and nitrogen in said coal.

40. The process of claim 38, wherein said potassium monosulfide is present in an amount at least stoichiometrically equal to said potassium pentasulfide.

41. The process of claim 37, wherein the alkali metal hydrosulfide is sodium hydrosulfide and the alkali metal polysulfide is sodium tetrasulfide and wherein the number of sulfur atoms in the sodium tetrasulfide above those of the sodium monosulfide ion is at least numerically equal to the number of atoms of oxygen, sulfur and nitrogen in said coal on a dry ashless basis and wherein the sodium hydrosulfide is present in at least stoichiometric equality with the sodium tetrasulfide present.

42. The process of claim 37, wherein the coal is lignite, sub-bituminous coal, low rank bituminous coal or oxidized higher rank coal.

43. The process of claim 37, wherein hydrogen sulfide is removed with an ethanol or methanol solution of an alkali metal hydroxide to constitute fresh reagent.

44. The process of claim 37, comprising using a mixture of potassium hydrosulfide and potassium pentasulfide in an alkanol.

45. The process of claim 37, wherein said steam is introduced after the temperature of the coal and reagent is above 100° C.

46. The process of claim 37, wherein the reagent consists of alkali metal hydrosulfide, alkali metal sulfides, and alkali metal polysulfides.

47. The process of claim 37, wherein the reagent consists of alkali metal hydrosulfides.

48. The process of claim 37, wherein the reagent consists of alkali metal sulfides.

49. The process of claim 37, wherein the reagent consists of alkali metal polysulfides.

50. The process of claim 37, wherein the reagent is alkali metal polysulfides and alkali metal monosulfides in which the said polysulfides are present in a quantity which is not greater than stoichiometrically equal to the monosulfides.

51. The process of claim 37, wherein said temperature is between 100° C. and 400° C.

* * * * *